United States Patent [19]
Burnhill

[11] Patent Number: 4,601,714
[45] Date of Patent: * Jul. 22, 1986

[54] VAGINAL DEVICE

[76] Inventor: Michael S. Burnhill, Rte. 24, R.D. 2, Mendham, N.J.

[ * ] Notice: The portion of the term of this patent subsequent to Jan. 14, 2003 has been disclaimed.

[21] Appl. No.: 586,875

[22] Filed: Mar. 7, 1984

Related U.S. Application Data

[63] Continuation-in-part of Ser. No. 511,759, Jul. 7, 1983, Pat. No. 4,564,362.

[51] Int. Cl.⁴ .................................................. A61M 31/00
[52] U.S. Cl. ......................................................... 604/286
[58] Field of Search ................ 604/286, 369, 904, 55, 604/58

[56] References Cited
U.S. PATENT DOCUMENTS

| | | | |
|---|---|---|---|
| 2,319,481 | 5/1943 | Stillman et al. | 424/285 X |
| 2,541,103 | 2/1951 | Sander | 424/318 |
| 2,759,931 | 8/1956 | Drake et al. | 548/230 |
| 2,774,709 | 12/1956 | Mayhew et al. | 424/170 |
| 2,902,484 | 9/1959 | Horclois | 544/44 |
| 2,927,110 | 3/1960 | Gever et al. | 544/137 X |
| 3,084,609 | 4/1963 | Dankwardt | 604/286 |
| 3,262,450 | 7/1966 | Elias | 604/55 |
| 3,762,414 | 10/1973 | Burnhill | 604/369 |
| 4,393,871 | 7/1983 | Vorhauer et al. | 604/58 |

Primary Examiner—William H. Grieb
Attorney, Agent, or Firm—Evelyn M. Sommer

[57] ABSTRACT

A vaginal device adapted for use as a disposable female contraceptive or as a disposable article for controllably dispensing drugs is provided comprising an outermost layer of resilient, compressible open-celled polymeric foam. Affixed to the outermost foam layer is a non-porous film layer made of a liquid proof, soft elastomeric material. Affixed to the non-porous film layer is another layer of open-celled polymeric foam. The intermediate film layer provides a barrier between the two foam layers. The outermost and innermost foam layers are formed from foams differing basically in density and/or number of pores per inch, with the more dense or smaller pored foam constituting the outermost layer, the outermost layer being adapted to lie against the cervix of the uterus and block the upper vaginal vault.

26 Claims, 9 Drawing Figures

VAGINAL DEVICE

This application is a continuation-in-part of application Ser. No. 511,759 filed July 7, 1983, now U.S. Pat. No. 4,564,362, granted Jan. 14, 1986.

This invention relates to a vaginal device and more particularly relates to a vaginal sponge used as a barrier contraceptive, as a carrier for a contraceptive or as a carrier and dispenser for medicaments. Still more particularly the invention relates to a disposable female contraceptive.

It is abundantly clear that one of the most crucial problems of man is the expanding population. Already the large cities are experiencing a disconcerting modern symptom of being "people trapped." What is more, the Malthusian nightmare of population exceeding the food supply has become a reality. Major efforts have been directed to thwart this crisis. The development of the oral contraceptive—i.e., the "pill" has been hailed as one of the major discoveries of our age and more significant to the human race than the release of atomic energy or space flights.

Unfortunately, there are side effects and certain risks involved in the taking of oral contraceptives. From 15 to 35% of the women using the oral contraceptives experience undesirable side effects. Nausea, vomiting, breast fullness, mastalgia, headache, dizziness, depression, apathy, fatigue, pelvic pain and chloasma are the most frequent. Fluid retention and weight gain are also observed. Thrombophlebitis has been the cause of greatest concern to the profession, the FDA and the public. Instance of jaundice have been reported. There has been some indication that contraceptive therapy may increase the blood pressure in a segment of the patients.

There are other contraceptive products available. They vary in mode of application, time of application, nature of device, cost, adverse affects and reliability. For the purpose of this disclosure, there may be mentioned the diaphragm, the cervical cap, foams, jellies, suppositories and the vaginal sponge.

The diaphragm and cervical cap involve the intervention of a physician and are expensive and in the case of the cervical cap may produce discomfort, infection and other problems. The foams, jellies and suppositories do not require a physician, are inexpensive and have the disadvantages that they are unpleasant and/or messy to use and have reliabilities of 85% or less.

It has already been proposed (U.S. Pat. No. 3,262,450) to use as a birth control method foam producing spermicidal compositions which are topically applied with cellular sponge of polyurethane plastic in which the average pore size does not exceed 1.5 mm. A foam producing material is introduced into the device which is termed "a topical application." Just prior to use the foam is produced by compressing and expanding the sponge and then this foam filled application is introduced into the vaginal cavity. Such structure possesses several deficiencies, including the already mentioned messiness of foams and more important that the applicator can not retain the spermicide containing foam any great length of time and thus has limited long term applicability.

A vaginal sponge contraceptive has been disclosed in U.S. Pat. No. 3,762,414 issued in 1973 to the inventor named herein. This sponge is a compressible, smooth surfaced, plastic sponge in the form of a solid rectangle, cylinder, sphere or the like and as disclosed is divided into two or more sections by a plastic, latex or other rubber sheet or film. The dividing sheet or film prevents the flow of fluid from one section of the sponge to the other. The sponge is used for controlling the flow of seminal fluid (contraception) and for dispensing medicaments.

The use of the sponge as a contraceptive is enhanced by incorporating into the sponge a spermicidal agent as, for example, a copper salt. Still further, the sponge as described in the patent may be used as a carrier and dispenser for medicaments, for example, as are used to treat infections.

As disclosed in U.S. Pat. No. 3,762,414, the vaginal sponge is produced from polyurethane foam or other smooth surfaced plastic foam and is divided into at least two sections separated by a plastic latex or other non-porous fluid impervious film. The contraceptive action is provided by sponge-like absorption of sperm by the foam material and blockage of the passage of such sperm by the film used to separate the sponge sections. Contraception is enhanced by the use of a chemical contraceptive which is absorbed and released in a sponge-like controlled manner.

Recently a non-prescription sponge contraceptive has been disclosed (V.L.I. Corporation of Costa Mesa California) which is round in shape and which is adapted to release a chemical, nonoxynol-9 that inactivates sperm. The V.L.I. sponge contraceptive is formed by foaming a contraceptive surfactant and a foam forming polymeric material or a monomer or prepolymer thereof. According to V.L.I. the polymerized foam substantially encapsulates the contraceptive surfactant so that the same will be slowly released for use only in those cases where the surfactant is present in large enough amounts i.e., greater than 10% of the dry weight of the sponge. If present in an amount less than 10% of the dry weight of the sponge, an organic fibril such as collagen must be added to help encapsulate the contraceptive agent.

This sponge, as in the case of the device disclosed in U.S. Pat. No. 3,762,414, also blocks the cervix and also acts to trap and absorb semen. As described by the press, "in clinical trials, the sponge was found to be about 85% effective in preventing pregnancy."

It is an object of the present invention to provide a multi-purpose vaginal device suitable for use in contraception and medicament application improved as compared to the state of the art with respect to consumer acceptance, efficacy and production feasibility.

A further object of the invention is to provide a multi-purpose vaginal device that completely prevents fluid flow from one of its ends to the other and yet is porous and absorbent.

Still a further object of the present invention is to provide a vaginal contraceptive device having an improved effectiveness in preventing pregnancy.

Yet a further object of the invention is to provide a vaginal device of the type described which may be economically mass produced and which may be simply packaged to facilitate storage and transportation thereof prior to use.

Another object of the invention is to provide a vaginal device of the type described for controllably dispensing drugs.

Still another object of the invention is to provide a vaginal device of the type described in which access is provided to the device for easy removal thereof.

These and further objects and advantages of the invention will be made clear or will become apparent during the course of the following description.

In accordance with the present invention a vaginal device is provided the outermost layer of which is an open-celled polymeric foam. Affixed to the outermost foam layer is a non-porous film layer made of a liquid proof, soft elastomeric material. Affixed to the non-porous film layer is another layer of open-celled polymeric foam. The intermediate film layer provides a barrier between the two foam layers. The outermost and innermost foam layers are formed from foams differing basically in density and/or number of pores per inch, with the more dense or smaller pored foam constituting the outermost layer, the outermost layer being adapted to lie against the cervix of the uterus.

The contraceptive action is provided by sponge-like absorption of sperm by the foam and blockage of the passage of such sperm by suitable selection of the foam and by the film used to separate the outermost and innermost sponge layers. The effectiveness of the device is enhanced by the introduction of a chemical contraceptive into at least one of the sponge layers, preferably during the manufacturing process for retention therein and from which it is absorbed and released in a sponge-like controlled manner. The presence of the spermicide serves to improve the device's effectiveness as a contraceptive.

When the device is used as an article for controllably dispensing drugs, it can be appreciated that the same or different drugs can be introduced into at least one of the sponge layers and that these drugs may be adapted for rapid release or for release over a prolonged period of time. The device of the invention thus permits the retention and therewith timed release application of medicaments or drugs.

In the drawings which form an integral part of the specification and are to be read in conjunction therewith, and in which like parts are designated by like numerals in the various views.

Figure 1:
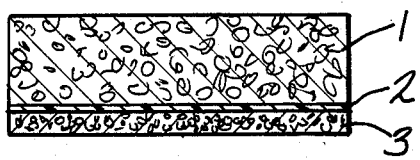
FIG. 1 is a sectional view of the vaginal device of the invention.

The device as constructed is a three dimension structure cylindrical in shape and preferably forms a more or less circular unit having a diameter of about 2 to 2 3/5 inches and a depth of about ⅝ to ¾ inches. The invention is not limited to the foregoing dimensions, the same being illustrative only. Thus, the device may also be spherical or globular in shape or may take the form of a truncated cone. Its diameter may decrease somewhat but this aspect is limited as it is critical that the device form a barrier across the vaginal canal. Its depth may increase, however, to include dimensions of up to about 3 3/5 inches.

The outermost and innermost layers should have a thickness of from about ⅛ inch up to about 1¾ inch each. Preferably the outermost layer is about ⅜ inch thick and the innermost layer about ⅛ inch thick. Such thicknesses insure ready impermeability yet also provide flexibility.

The barrier film should have a thickness of about 0.5 to about 3 mils, preferably from 1 to 2 mils.

As noted hereinabove, the device in use must be positionable to close the cervical opening and for sealingly abutting the walls of the vaginal canal.

The foam must of course be biocompatible, non-toxic and non-irritating and is preferably a polyurethane foam. In addition the foam must be natural and soft in feeling so that the user in the case of medical application and in the case of contraceptive use, neither sexual partner is aware of its presence. Any polyurethane foam which can be fabricated with the characteristics needed for the intended end use (soft, pliable, flexible, porous) may be employed.

While the polyurethane foams are preferable, there are not presently any reasons why the polyester, polyether, polyethylene, crosslinked polyethylene and the like combination foams, as for example polyester-polyurethane foams may not be used. The criteria for selection of course must include in addition to effectiveness, safety for their intended use.

Preferably, the foams are open cell, but it would appear that closed cell foams would work as well. The cell structure most preferably is open cell, 80–200 pores per inch. The density of the foam will vary as hereinafter described but can range from 1.5 to 3.0 lbs. per cu. ft. and even higher.

The tensile strength characteristics are somewhat important and should amount to about 30–39 psi. It can be appreciated that the foams involved are readily available and that there is no difficulty envisioned should there be a need to custom fabricate so as to produce the desired characteristics.

Most important, the sponge must be permeable, it must be capable of absorbing, retaining and then releasing a spermicide or medicament. At the same time, it must be a barrier for the microsized highly mobile sperm. In this case, the pore size is critical not only for barrier effectiveness but for ensuring retention of the spermicide or medicinal agent for any appreciable period.

Foams marketed under the trade names Scott Industrial Foam, Scottfelt Foam, Pyrell and the like are particularly suitable for use in producing the device of the invention. Two foams are used in constructing the instant device with the foams being selected so as to provide layers of differing resiliency, stiffness and absorbency. The density and cell structure, particularly the pores per inch, determine the characteristics. As noted above the more dense or smaller pored foam is selected for forming the outermost layer.

The foam layers are separated one from the other by a barrier film. The film barrier can be made of natural rubber, synthetic rubber or latex material, or other elastomeric material. It is also possible to use a barrier layer certain of the laminated packaging materials, as for example a barrier coextruded layer comprised of a two or three layer combination of ethylene methacrylate copolymer and polyester. It is contemplated that in place of the barrier film a glue layer may be used. As glue there may be used any suitable adhesive i.e., one which is pharmacologically acceptable and capable of forming an impervious layer. An example of such an adhesive layer is a polyolefin adhesive layer. Another adhesive which may be used is ethylene acrylic acid.

The layers of sponge are so arranged as to provide an outermost layer forming an expansion collar which aids in securing the device, holding the device in position, and which furthermore reinforces the barrier effect of the film and of the innermost sponge layer.

The use of a string or thread or woven fabric ribbon is contemplated for facilitating removal and/or withdrawal of the device. Alternate removal means may be substituted as for example tab means applied with a biocompatible adhesive on the exposed surface and capable of being grasped and/or held while the device is being removed.

Accordingly, it can be appreciated that the use of the urethane-barrier film or adhesive layer sponge device per se without the addition of a spermicidal agent is contemplated as reliable for contraceptive use.

However, the efficacy is improved when the sponge (one or both layers) for contraceptive use is impregnated with a spermicide, preferably during the manufacturing process, such as nonoxynol-9, which has long been recognized as safe and effective for this purpose. Other examples of spermicides which are suitable for use herein include nonylphenoxypolyethoxyethanol, methoxypolyoxyethyleneglycol 500 laureate, stearic acid, ricinoleic acid, p-diisobutylphenoxyethoxyethanol, p-menthanylphenylpolyoxyethylene ether, octylcresolpolyoxyethylene ether, polyoxyethylene oxypropylene stearate, polyoxyethylene laureate, glycerol ricinolate, triisopropyl phenylpolyoxyethylene ether, mono-iso-octyl phenyl ether, polyethylene glycol, polyoxyethylene stearylamine, benzalconium chloride, sodium dodecylsulfate, sodium oleate, zinc phenolsulfonate, dodecylbenzene sulfonate, dodecyl diaminoethyl glycine, and the like.

The spermicide is required to be present in an amount of 1% to 10% and preferably 2% to 3%.

No preservatives or pH reducers should be required but if they are added, it is well within the skill of the art to determine in what amounts the same may be present.

Instances of preservatives include benzoic and sorbic acid.

An example of an agent which may be added to lower the pH is citric acid. The pH in the vagina is approximately 4.0 to 5.0. If the vaginal pH is increased to any extent above this range, the growth of bacteria is encouraged. The citric acid can be added in an amount whereby the pH of the solution in the sponge is below that of the vaginal pH and namely below 4.0 and preferably at about 3.5.

In addition to the spermicide or in place thereof, pharmaceuticals such as antibiotics, antifungals, antibacterials, steroids, etc., may be added to the solution, of which more detail will be given later, and incorporated into the sponge.

Thus, and this is most important, the sponge may be used as means for dispensing medicaments as for example, anti-infection agents, anti-microbials, hormones, enzymes, psychotropic drugs, cardiac and blood pressure regulators, etc. This aspect of the invention is considered to be a very important one. Further, the medicament itself or the medicament and sponge may be modified for controlled or timed release during use.

Illustrative of the suitable medicaments and the categories in which they fall are the following:

| Name | Category |
| --- | --- |
| aminophylline | smooth muscle relaxant |
| aspirin | analgesic |
| conjugated estrogen ethinylestradiol | estrogen |
| iodochlorhydroxyquin | local anti-infective |
| metronidazole | anti-trichomonal |
| sulfisoxazole | antibacterial |
| miconazole | anti-fungal |
| prochlorperazine | tranquilizer |
| nilstat | anti-yeast and anti-Candida |

Other medicaments which can be mentioned are barbital, chloralhydrate, cocaine hydrochloride, digitalis leaf, phenobarbital, procaine, sulfanilamide, sulfathiazole, sulfonal and the like.

The medicaments can be introduced into the sponge layers during the manufacturing process, singly or in combination, into one or both of the layers, as afore noted in a rapid release, or relatively long duration or prolonged release form. Preferably, the spermicide in the form of 2 to 3% aqueous solution is delivered into the sponge to provide a sponge having a nonoxynol weight content of 100 to 500 mg and preferably 200 to 300 mg.

The vaginal sponge of the invention can be fabricated by any of the conventional foam techniques. The incorporation of the film between the two foam layers is known, as are the techniques for making the foams. Any of the known methods of molding, extrusion, stamping, etc., may be used singly or in combination to make the device. To the same end, the conventional techniques for loading the sponge with spermicide and/or medicament for storage and controlled release thereof may be employed.

Products that are intended to provide prolonged therapeutic action after administration are known. These products are variously described as being "sustained release," "timed release," "prolonged action", "long acting," or by simple terms implying an extended period of action for a given drug in some special dosage product.

It is evident that products intended to provide for extended action of drug from a single dose may be considered "convenience dosage forms" by virtue of eliminating the necessity for dosage several times during the day. However, therapeutic benefits may also be obtained and therefore should be considered as being more than "convenience dosage forms."

There are included as coming within the scope of the invention the following drug dosage forms:

Encapsulated slow release beads

In this dosage form, the dose is divided into 2 to 10 portions and a different number of coats or thickness of coats applied. The coating is resistant to but soluble in body fluid.

The Spansule ® type of encapsulated coated pellets is illustrative of this dosage form. The dose is divided into 3 to 9 parts, one part of any given dose so divided is intended to establish mutual therapeutic level and the remaining parts being the sustained release dose. For example the dose is divided into four equal parts, one part uncoated beads, the next part with a coating to resist disintegration for three hours, the next with a six hour coating and the last with a nine hour coating.

Beads

The drug can be mixed with a material such as a shellac in order to provide a mass from which the drug is leached out of when the beads are in contact with the fluid at the absorption site.

Small cylindrical slow release beads can be prepared by extruding mixtures of the drugs and material such as zain or kafir.

Beads with slow release cores

In this case the beads consist of a core containing the therapeutically active material evenly mixed in a mixture of substantially non-absorbable but capable of slow dissolution or loss of drug by leaching and an outer layer which is compressed onto the core and which also contains therapeutically active material.

As active ingredient for the bead or spansule form of preparation there may be mentioned:
(1) methscopolamine bromide methobarbital
(2) atropine sulfate and phenobarbital
(3) amphetamine sulfate
(4) isopropamide and prochlorperazine
(5) prochlorperazine sulfate
(6) d-amphetamine sulfate
(7) reserpine
(8) d-amphetamine and prochlorperazine
(9) vitamins A, $B_1$, $B_2$, $B_6$, C, nicotinamide and pantothenic acid
(10) diphenylpyraline
(11) meprobromate
(12) pentaerythritoltetra nitrate
(13) belladonna alkaloids
(14) chlorpheniramine maleate

Ion exchange resins

In ion exchange resins, the action from preparations found on ion exchange resin is presumed to result from the slow rate of displacement reaction when drug-resin contacts body fluid and the ionic constituents are dissolved therein. This is illustrated by the equation where a sulfonic acid type cation exchange resin combined with a basic drug B is contacted with vaginal fluid.

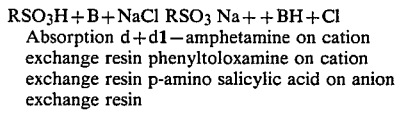

Absorption d+dl—amphetamine on cation exchange resin phenyltoloxamine on cation exchange resin p-amino salicylic acid on anion exchange resin

Slightly soluble salts or complexes

The preparation of salts or complexes of active drugs that are only slightly soluble in body fluid may produce a compound that results in a prolonged action when used in appropriate dosage form.
Illustrative of this form are the following:
atropine tannate
quinidine polygalacturonate
phenylephrine tannate, prophenpyridiamine tannate and pyrilamine tannate
d-amphetamine $PO_4$ and caffeine
Cryptenamine tannate

Liquid Preparations

These products incorporate the prolonged release principles discussed above. For example, the liquid preparation may be a suspension of drug on ion exchange resin.

Initially prepared materials are mixed with a dissolution retarding material and suspended in a suitable aqueous medium.

Examples of drugs used in this form are:
sulfadiazine
N'-acetylsulfisoxazole
sulfamerazine
sulfadiazine
phenylephrine, prophenpyridamine+pyrilamine as tannates
sulfamethylthiadiazole The method of manufacture of the end product polymer sponge must encompass its packaging as it is critical with a product of this type that the product be delivered in a sanitary or sterile form. A number of packaging methods are contemplated including the use of barrier laminates such as are presently used in connection with liquid, food, cosmetic and medical products. The sponge, prior to introduction of the spermicide and/or medicinal agent or after such step is completed, is placed on a sheet of barrier film which is thereafter covered over with a further sheet of the same film and sealed on all four sides. If the packaging involves the use of an envelope or bag sealed on three sides or even one side, the respective sides not so sealed can thereafter be sealed using an adhesive if necessary or by relying on the heat seal nature of the barrier film itself. It is contemplated that in place of heat, ultrasound, RF or other form of sealing techniques can be used. The atmosphere, materials and other precautionary measures are observed to provide a sterile packaged sponge. What results is a packet of the type known in the art for retaining a moist, wet product for prolonged periods of time having a long shelf life, yet easily opened when needed.

Referring to FIG. 1, an outermost layer 1 of open cell polyurethane foam having about 150 psi and having a thickness of about ⅜ inch is affixed to a latex film 2 having a thickness of about 1.5 mils. The innermost layer is an open cell polyurethane foam 3 having about 100 psi and having a thickness of about ⅛ inch. The device is a cylindrical construction having a diameter of about 2-3/5 inches and a thickness just exceeding ¾ inches.

Figure 2:
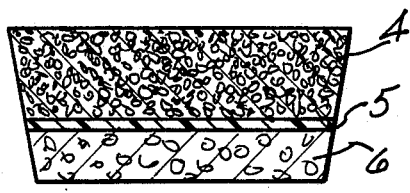
FIG. 2 is a sectional view of an alternate form of the vaginal device of the invention.

As illustrated in FIG. 2, the device is of a truncated cone construction composed of two different foams, a more dense foam 4 i.e., Scottfelt foam having a density of about 3 lbs/cu. ft. separated by a latex film barrier layer 5 from a less dense foam layer 6 i.e., Scott Industrial Foam (fine porosity) having a density of about 1.75 lbs. per cu. ft. The total thickness of the construction is about 1 inch. The outermost layer of more dense foam is about twice as thick as the innermost layer. The latex film is approximately 2.0 mils in thickness.

Figure 3:
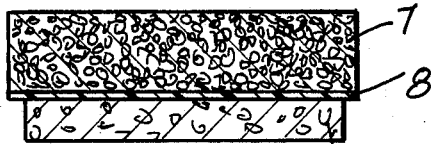
FIG. 3 is a sectional view of yet another form of the vaginal device of the invention.

In the construction shown in FIG. 3, a sponge device is provided in which the edge of the more dense layer of foam 7 protrudes slightly beyond the edge of the less dense sponge layer 9. The barrier film layer 8 extends over the entire inner edge of the layer 7. In this instance layer 7 is made of Pyrell (polyester), has a density of about 3.0 lbs/cu. ft. and layer 9 is made of a less dense Pyrell i.e., having a density of 2.5 lbs./cu. ft.

As illustrated, this edge composed of the more dense foam but still resilient and flexible sponge, is partially compressed during the act of insertion. It is the outward pressure of this sponge layer that produces a gentle but effectual grasping and retention of the device contributing in no small measure to its increased effectiveness.

Figure 4:
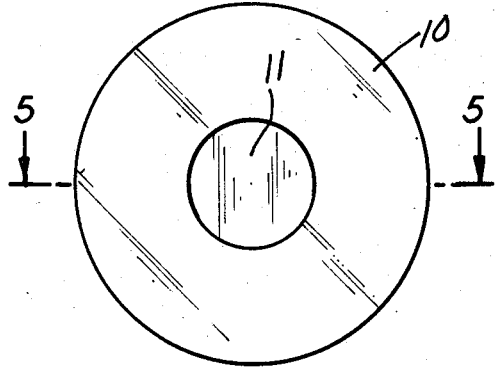
FIG. 4 is a plan view of still another form of the vaginal device of the invention.
Figure 5:
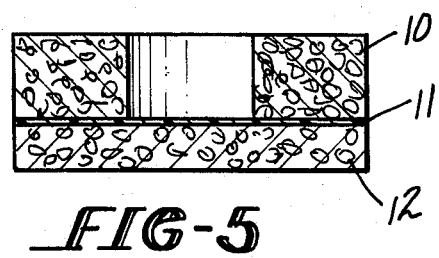
FIG. 5 is a sectional view taken along the line 5—5 in FIG. 4.

The embodiment shown in FIGS. 4 and 5 is a particularly preferred vaginal contraceptive construction. In this instance the topmost or outermost layer 10 is constructed in the form of an "O" ring, the barrier layer 11 being exposed at the center portion thereof. However, the barrier layer and the innermost layer are continuous. The result of this construction is that while the barrier across the vaginal canal is retained the device is particularly well adapted to lie against the cervix of the uterus and the edges of the outermost layer 10 being adapted to block the vaginal fornices.

While the device constituting my invention has been described as being more or less circular in shape, other shapes, i.e., elliptical, pear and the like, are contemplated.

In the same manner, while the device has been disclosed as consisting of two (2) layers of sponge separated by a layer of impervious film, it is of course possible to have additional layers of sponge. However, at least one layer of impervious film must be present and disposed between two layers of sponge, i.e., only one layer of impervious film is required, regardless of how many foam layers are present.

Figure 8:
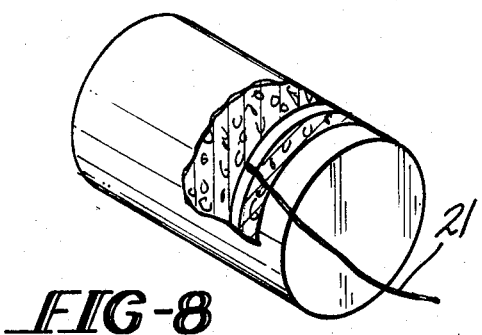
FIG. 8 is a perspective view showing another embodiment of the invention directed toward facilitating removal of the device.

In FIG. 8, the device as shown is composed of two layers, with a total thickness of about 2 inches. In the embodiment for facilitating removal, a withdrawal string 21 made of cotton or nylon thread is provided. In place of the string a woven or non-woven tape may be substituted.

Figure 6:
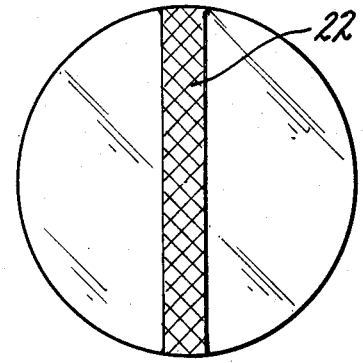
FIG. 6 is a plan view showing a strip attachment for facilitating removal of device after use.
Figure 7:
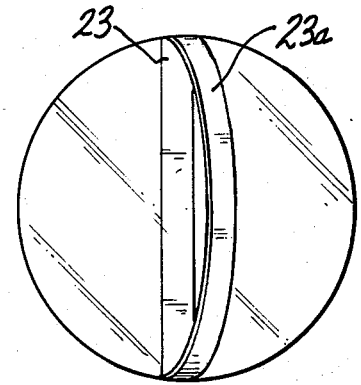
FIG. 7 is a plan view showing yet another type of attachment for use in removal of the device.

FIG. 6 and 7 illustrate alternate means for faciliating removal of the device. In FIG. 6 a strap 22 made of a woven natural non-irritating material is provided, while in FIG. 7 a flap 23 of a non-irritating material is provided. The flap is provided with a free end 23a which can be grasped for withdrawal of the device.

Figure 9:
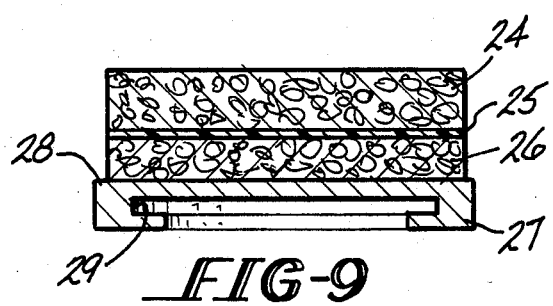
FIG. 9 is a sectional view of a further embodiment of the invention directed toward facilitating removal of the device.

As illustrated in FIG. 9, in addition to the foam and film barrier layers 24, 25 and 26, a flange like layer of dense foam 27 which can be open or closed cell such as a layer of Volara (cross-linked polyethylene foam) having a density of about 5 lbs per cu. ft. is affixed to the innermost layer 26. The layer 27 is fabricated to provide a finger gripping area 28 and/or 29. The flange layer in this instance is about ¼ inch in thickness. It can be appreciated that while a continuous flange is shown in the drawing the flange section can be provided as a one-sided structure.

As a further embodiment, it is contemplated that a layer of suitable adhesive (pharmacologically acceptable and forming an impervious barrier layer) may be substituted for the elastomeric film layer in any of the above embodiments.

The following examples are given in order to more fully illustrate the invention and are not to be construed as limitative thereof:

EXAMPLE 1

During the process of manufacture of a device as shown in FIG. 3 there is incorporated into both foam layers 4 and 6 the spermicide nonoxynol-9 (poly(ethyleneglycol) p-nonyl phenylether). This compound is known (U.S. Pat. No. 2,541,103) and its preparation is disclosed in U.S. Pat. No. 2,774,709. The nonoxynol-9 is dissolved in water so as to form a 2.5% solution. 10 ml of this solution are delivered to the sponge to provide 250 mg of spermicide.

EXAMPLE 2

During the process of manufacture, there is incorporated into a device as shown in FIG. 4, prochlorperazine (2-chloro-10-[3-(4-methyl-1-piperazinyl)-propyl]-10H-phenothiazine. This compound is a known tranquilizer. Its preparation is described in U.S. Pat. No. 2,902,484. 5 mg prochlorperazine edisylate are dissolved in 5 ml of water and this solution introduced into both layers of sponge so as to provide 250 mg of active agent.

EXAMPLE 3

In place of prochlorperazine, a combination of furazolidone (3[[5-nitro-2-furanyl)methylene]-amine]-2-oxazolidinone) (U.S. Pat. Nos. 2,759,931 and 2,927,110) and nitrofuroxime (5-nitro-2-furancarboxaldehyde oxime) (U.S. Pat. No. 2,319,481), both known anti-bacterials and antiprotozoan compounds are incorporated into the device described in Example 2 and resulted in a markedly effective anti-effective antibacterial and antiprotozoal agent.

The same desirable results were realized when the foregoing combination was replaced by metronitazole (Searle) having trichomonical and antibacterial effectiveness.

The active agent in this case was present in an amount of 250 mg.

As described above, the medicaments and spermicide are dispersed from the surface of the device into the surrounding medium. As the medicament or spermicide is removed from the surface further amounts migrate to the surface until the supply of spermicide or medicament is exhausted.

It is well within the skill of the art to control the rate of dispensing so as to provide the active agents as indicated for conventional and/or prolonged release forms.

It is also believed that the artisan and the user are well aware of how the device is to be inserted and removed and that accordingly the details therefore need not be expressly set forth.

I claim:

1. A vaginal device comprising an outermost layer of resilient compressible, open-celled, polymeric foam, a non-porous film layer formed of a liquidproof, soft elastomeric material affixed to said outermost foam layer, and a second layer of open-celled polymeric foam affixed to the opposite surface of said non-porous film layer, said outermost and innermost foam layers differing in density and/or numbers of pores per inch with the more dense or smaller pored foam layer constituting the outermost layer, said outermost layer being adapted to lie against the cervix of the uterus, said device having a diameter of about 2-2 3/5 inches and thickness of up to about 3 3/5 inches.

2. A vaginal device according to claim 1, wherein said device is a three-dimensional structure cylindrical in shape.

3. A vaginal device according to claim 1 wherein said device is a three dimensional structure globular in shape.

4. A vaginal device according to claim 1 wherein said device is a three-dimensional structure having the shape of a truncated cone.

5. A vaginal device according to claim 1 wherein said outermost and innermost layers have a thickness of from about ⅛ inch up to about 1 ¾ inch each.

6. A vaginal device according to claim 5 wherein said outermost layer is about ⅜ inch thick and said innermost layer is about ⅛ inch thick.

7. A vaginal device according to claim 1 wherein said barrier film has a thickness of about 0.5 to about 3 mils.

8. A vaginal device according to claim 7 wherein said barrier film has a thickness of about 1 to 2 mils.

9. A vaginal device according to claim 1 wherein said foam layers are fabricated of a member selected from the group consisting of polyurethane, polyester, polyether, polyethylene foams and combinations thereof.

10. A vaginal device according to claim 9 wherein said foam is a polyurethane foam.

11. A vaginal device according to claim 10 wherein said foam is an open-cell foam having 80–200 pores per inch.

12. A vaginal device according to claim 1 wherein said non-porous film layer is a barrier film made of natural rubber, synthetic rubber, or latex material.

13. A vaginal device according to claim 1 wherein said non-porous film layer is a glue layer made of a pharmaceutically acceptable adhesive.

14. A vaginal device according to claim 1 wherein said non-porous film layer is made of a barrier laminate.

15. A vaginal device according to claim 1 provided with means for facilitating removal and/or withdrawal of the device.

16. A vaginal device according to claim 1 adapted for use as a contraceptive.

17. A vaginal device according to claim 16 wherein at least one of said foam layers is impregnated with a spermicide.

18. A vaginal device according to claim 16 wherein said spermicide is nonoxynol-9.

19. A vaginal device according to claim 17 wherein said spermicide is present in an amount of one to ten percent.

20. A vaginal device according to claim 16 wherein at least one of said layers is additionally impregnated with at least one member of the group consisting of preservatives, ph reducers, antibiotics, antifungals, antibacterials and antimicrobials.

21. A vaginal device according to claim 1 adopted for use as a medicament dispenser.

22. A vaginal device according to claim 21 wherein at least one of said foam layers contains at least one member selected from the group consisting of antibiotics, antifungals, antibacterials, antimicrobials, hormones, enzymes, psychotropic drugs, cardiac and blood pressure regulators, analgesics and antipyretics.

23. A vaginal device according to claim 22 wherein said group member is modified for controlled or time-release of said group member during use.

24. A vaginal device according to claim 1 packed and sealed in an envelope of barrier film material under sterile conditions.

25. A method for providing contraception which comprises inserting a vaginal device according to claim 1 into the vagina of the female subject prior to intercourse so that the outermost layer lies against the cervix of the uterus and blocks the upper vaginal vault.

26. A method for dispensing drugs or other medicaments which comprises inserting a vaginal device according to claim 22 into the vagina of the female subject requiring treatment with the drug incorporated into at least one of said foam layers.

* * * * *